(12) United States Patent
Suzuki et al.

(10) Patent No.: US 8,267,517 B2
(45) Date of Patent: Sep. 18, 2012

(54) EYEBALL MOTION MEASUREMENT APPARATUS

(75) Inventors: Kazutaka Suzuki, Hamamatsu (JP);
Haruyoshi Toyoda, Hamamatsu (JP);
Munenori Takumi, Hamamatsu (JP);
Naohisa Mukozaka, Hamamatsu (JP)

(73) Assignee: Hamamatsu Photonics K.K.,
Hamamatsu-shi, Shizuoka (JP)

( * ) Notice: Subject to any disclaimer, the term of this patent is extended or adjusted under 35 U.S.C. 154(b) by 210 days.

(21) Appl. No.: 12/744,711

(22) PCT Filed: Nov. 7, 2008

(86) PCT No.: PCT/JP2008/070333
§ 371 (c)(1),
(2), (4) Date: Jul. 29, 2010

(87) PCT Pub. No.: WO2009/069451
PCT Pub. Date: Jun. 4, 2009

(65) Prior Publication Data
US 2010/0309432 A1   Dec. 9, 2010

(30) Foreign Application Priority Data

Nov. 29, 2007  (JP) .................................. 2007-308944

(51) Int. Cl.
*A61B 3/14* (2006.01)
(52) U.S. Cl. .......................... 351/210; 351/206; 351/209
(58) Field of Classification Search .................. 351/209, 351/210
See application file for complete search history.

(56) References Cited

U.S. PATENT DOCUMENTS

| 7,789,838 B2 * | 9/2010 | Merfeld et al. | 600/559 |
| 8,025,404 B2 * | 9/2011 | Bolger et al. | 351/209 |
| 2011/0116045 A1 * | 5/2011 | Utagawa | 351/210 |

FOREIGN PATENT DOCUMENTS

| JP | H4-193255 | 7/1992 |
| JP | 4-242628 | 8/1992 |
| JP | 3724524 | 9/2005 |
| JP | 2008-099716 | 5/2008 |
| WO | 02/43613 | 6/2002 |

OTHER PUBLICATIONS

N. F. Sheahan et al., "Ocular microtremor measurement system: design and performance", Medical and Biological Engineering and Computing, 31, pp. 205-212 (May 1993).
C. Bolger et al., "Ocular micrometer in patients with idiopathic Parkinson's disease", J. Neural Neurosurg Psychiatry, 66, pp. 528-531 (1999).

* cited by examiner

*Primary Examiner* — Jordan Schwartz
(74) *Attorney, Agent, or Firm* — Drinker Biddle & Reath LLP

(57) ABSTRACT

An eye movement measurement apparatus 1 measures movement of a cornea 101 by imaging a corneal reflection light image L2 generated as a result of irradiating the cornea 101 with infrared light L1. The eye movement measurement apparatus 1 includes: an imaging section 5 having a sensor section 51 including a plurality of pixels arrayed two-dimensionally, for generating imaging data including the corneal reflection light image L2 made incident on the sensor section 51; a bright spot position operation section 6 that calculates a position of the corneal reflection light image L2 in the imaging data; and a tremor signal operation section 7 that generates a third data string indicating a tremor component included in movement of the cornea 101 by calculating a difference between a first data string concerning temporal changes in position of the corneal reflection light image L2 and a second data string obtained by smoothing the first data string. Accordingly, an eye movement measurement apparatus capable of accurately detecting a tremor component is realized.

8 Claims, 11 Drawing Sheets

EYEBALL MOTION MEASUREMENT APPARATUS

TECHNICAL FIELD

The present invention relates to an eye movement measurement apparatus.

BACKGROUND ART

Human eye movement includes rapid and minute movement (small involuntary eye movement), and the involuntary eye movement is categorized into the following three types of movement. That is, the three types of movement include drift that is small smooth movement at low frequency, flick that is small saccadic movement (also called microsaccade), and tremor that is very small high frequency oscillation. It has been said that the magnitude of involuntary eye movement varies according to tiredness, illness, and the like, and it has been reported, for example, that the magnitude of drift of a patient with dementia is different from that of a healthy person, and moreover, because tremor is not measured immediately before brain death, it has been considered that there is a close relationship between tremor and brain function.

There have been many attempts at measuring such small involuntary eye movement and applying the involuntary eye movement to estimate a human's state of consciousness and state of health. It has been described, for example, in Patent Document 1 that the degree of visual attention when gazing at a high-definition screen or the like can be found based on the magnitude of the involuntary eye movement. In addition, an eye control system information detection apparatus described in this document, for removing a tremor component that is a high-frequency component and becomes noise when extracting from the involuntary eye movement a drift component and a microsaccade component that are low-frequency movements, smoothens time series data concerning an eye movement.

Moreover, while a tremor component has been removed as noise in Patent Document 1 described above, information that can be estimated based on the tremor component has also been suggested. For example, in Non-Patent Document 1, the relationship between the tremor component and the brain stem has been suggested, and there has been proposed a contact measurement apparatus using a piezoelectric element, for applying a tremor component to an index to find the depth of sleep, coma, or anesthesia, an index of brain death, and the like. Moreover, in Non-Patent Document 2, it has been reported that a tremor component of a patient with Parkinson's disease is unique.

Patent Document 1: Japanese Patent No. 3724524
Non-Patent Document 1: N. F. Sheahan et al., "Ocular microtremor measurement system: design and performance", Medical and Biological Engineering and Computing, 31, pp. 205-212 (1993)
Non-Patent Document 2: Ciaran Bolger et al., "Ocular microtremor in patients with idiopathic Parkinson's disease", J. Neural Neurosurg Psychiatry, 66, pp. 528-531 (1999)

DISCLOSURE OF THE INVENTION

Problem to be Solved by the Invention

However, since tremor is very small high-frequency oscillation with an amplitude on the order of 1 μm, it is difficult to accurately detect tremor as compared with drift and flick (microsaccade). In Non-Patent Document 1, the piezoelectric element is pressed against the eye to attempt a measurement of tremor, but for use for an actual patient diagnosis, health diagnosis, or the like, a non-contact and simple, high-speed, high-accuracy measurement apparatus is desirable. Moreover, in Patent Document 1, there is no mention of estimation of these based on a tremor component, and there is also no disclosure at all of a method for accurately extracting only the tremor component.

The present invention has been made in view of the above-mentioned problems, and an object thereof is to provide an eye movement measurement apparatus capable of accurately detecting a tremor component.

Means for Solving the Problem

In order to solve the above-mentioned problems, an eye movement measurement apparatus according to the present invention, which is an eye movement measurement apparatus that measures movement of a cornea by imaging a corneal reflection light image generated as a result of irradiating the cornea with light, includes: an imaging section having a photodetecting section including a plurality of pixels arrayed two-dimensionally, for generating imaging data including the corneal reflection light image made incident on the photodetecting section; bright spot position operation means that calculates a position of the corneal reflection light image in the imaging data; and tremor signal operation means that generates a third data string indicating a tremor component included in movement of the cornea by calculating a difference between a first data string concerning temporal changes in position of the conical reflection light image and a second data string obtained by smoothing the first data string.

When imaging data including a corneal reflection light image is generated at a predetermined frame rate by the imaging section, a frame-by-frame position of the corneal reflection light image in this imaging data is calculated by the bright spot position operation means. Time series data to be thus obtained, that is, a first data string concerning temporal changes in position of the corneal reflection light image is time series data directly indicating movement of the eye, and includes both a component due to drift and flick (microsaccade) being low-frequency small involuntary eye movements and a component due to tremor being a high-frequency small involuntary eye movement.

Then, the first data string is smoothed in the tremor signal operation means to generate a second data string. The second data string, in which a tremor component has been removed by smoothing, includes mainly a drift component and a flick component. Therefore, by calculating a difference between the first data string and the second data string, the drift component and the flick component are favorably removed from the first data string, and a data string (third data string) including mainly the tremor component is obtained. Thus, according to the above-mentioned eye movement measurement apparatus, a drift component and a flick component can be removed from time series data concerning temporal changes in position of a corneal reflected light image to accurately detect a tremor component.

Effects of the Invention

According to the eye movement measurement apparatus of the present invention, a tremor component can be accurately detected.

DESCRIPTION OF THE SYMBOLS $D_1$—first data string, $D_2$—second data string, $D_3$—third data string, L1—infrared light, L2—corneal reflection light image, L3—visible light, Q—charge, 1—eye movement measurement apparatus, 2—lighting unit, 3—half mirror, 4—condenser lens, 5—imaging section, 6—bright spot position operation section, 7—tremor signal operation section, 8—measurement control operation section, 9—measurement control section, 11—indicator, 11a—lens, 51—sensor section.

BEST MODES FOR CARRYING OUT THE INVENTION

Hereinafter, an embodiment of an eye movement measurement apparatus according to the present invention will be described in detail with reference to the accompanying drawings. The same components are denoted with the same reference symbols in description of the drawings, and overlapping description will be omitted.

Figure 1:
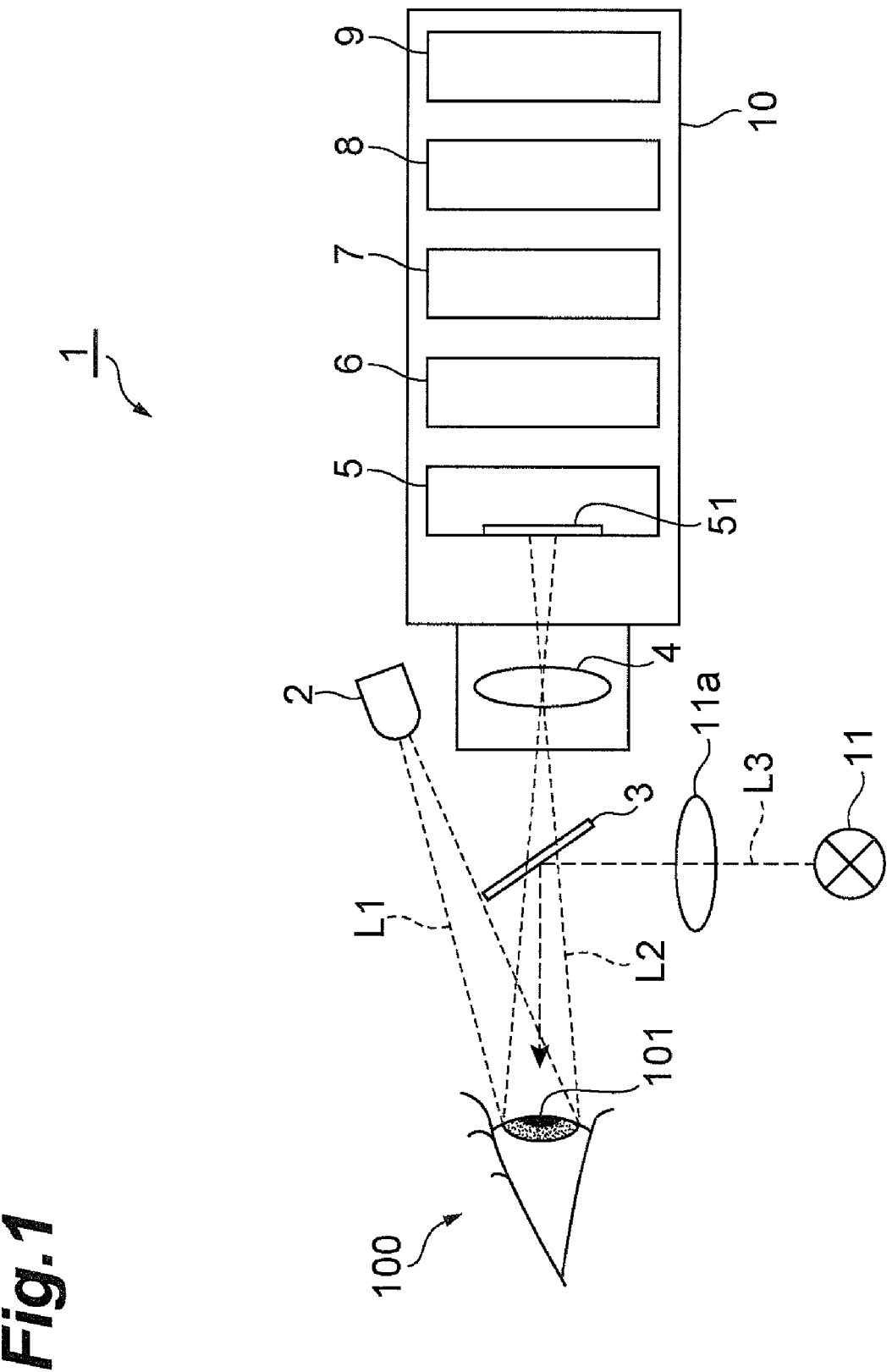
FIG. 1 is a schematic view showing an embodiment of an eye movement measurement apparatus.

FIG. 1 is a schematic view showing an embodiment of an eye movement measurement apparatus according to the present invention. Referring to FIG. 1, the eye movement measurement apparatus 1 according to the present embodiment includes a lighting unit 2, a half mirror 3, a condenser lens 4, an imaging section (imaging means) 5, a bright spot position operation section (bright spot position operation means) 6, a tremor signal operation section (tremor signal operation means) 7, a measurement control operation section 8, and a measurement control section 9. The condenser lens 4, the imaging section 5, the bright spot position operation section 6, the tremor signal operation section 7, the measurement control operation section 8, and the measurement control section 9 are stored inside of a measurement section (camera) 10.

The lighting unit 2 of the present embodiment includes, for example, an infrared LED. The lighting unit 2 is optically coupled to a cornea 101 of a subject's eye 100. By the lighting unit 2 irradiating the cornea 101 with infrared light L1, the infrared light L1 is reflected on the cornea 101 to generate a corneal reflection light image L2.

In addition, a light source of the lighting unit 2 is not limited to an infrared LED and another light source can be used, but since it is too bright for the subject if the amount of light is increased when a visible light source is used, an infrared light source is preferably used. Moreover, the lighting unit 2 may include a plurality of infrared LEDs provided at positions different from each other. In such a case, any one of the infrared LEDs selected by the measurement control operation section 8 to be described later is controlled so as to emit light by the measurement control section 9.

The half mirror 3 is disposed so as to transmit the corneal reflection light image L2 and make the corneal reflection light image L2 be incident into a sensor section (photodetecting section) 51 of the imaging section 5. Moreover, the half mirror 3 optically couples an indicator 11 placed beside an optical axis connecting the cornea 101 and the imaging section 5 and the cornea 101 so that the indicator 11 is visible to the subject. The indicator 11 is, for example, by combination of a plurality of LEDs to generate visible light and a pinhole mask, formed so as to generate a plurality of bright spot patterns different in position from each other. Any one of the bright spot patterns is selected by the measurement control operation section 8 to be described later, and an LED corresponding to this bright spot pattern is selectively controlled so as to emit light by the measurement control section 9. In addition, the indicator 11 may be formed by, besides such a configuration, for example, an image display device such as a liquid crystal panel, a rotating plate, and the like.

The half mirror 3 reflects visible light L3 emitted from the indicator 11 toward the eye 100. This allows presenting the indicator 11 to the subject to stabilize the position of the cornea 101, while imaging the cornea 101. It is more preferable that an eyesight adjustment lens 11a is provided between the indicator 11 and the half mirror 3. A focus of the indicator 11 to be determined by this lens 11a is determined by the measurement control operation section 8 to be described later, and controlled by the measurement control section 9.

The condenser lens 4 is a lens for condensing an optical image L2 to form an image on the sensor section 51 of the imaging section 5. The condenser lens 4 is disposed between the half mirror 3 and the imaging section 5.

The imaging section 5 is means for imaging the corneal reflection light image L2 at a predetermined frame rate. The imaging section 5 has the sensor section 51 including a plurality of pixels arrayed two-dimensionally, and converts the corneal reflection light image L2 made incident on the sensor section 51 to an electrical signal in each pixel to thereby generate imaging data indicating the amount of incident light per pixel concerning the corneal reflection light image L2. The imaging section 5 outputs the generated imaging data to an output unit such as a display device or an image output terminal, and provides the imaging data to the bright spot position operation section 6.

The bright spot position operation section 6 calculates an incident position of the corneal reflection light image L2 in the imaging data provided from the imaging section 5 frame by frame to generate information concerning the position of the corneal reflection light image L2, that is, a bright spot (bright spot position information). Moreover, the tremor signal operation section 7, based on the bright spot position information provided from the bright spot position operation section 6, generates a first data string concerning temporal changes in position of the corneal reflection light image L2 and a second data string obtained by smoothing the first data string. Then, the tremor signal operation section 7, by calculating a difference between the first and second data strings, generates a third data string indicating a tremor component included in movement of the cornea 101.

In addition, the bright spot position operation section 6 and the tremor signal operation section 7 may be realized either as electrical circuits or as software inside a computer having a central processing unit and a memory.

Figure 2:
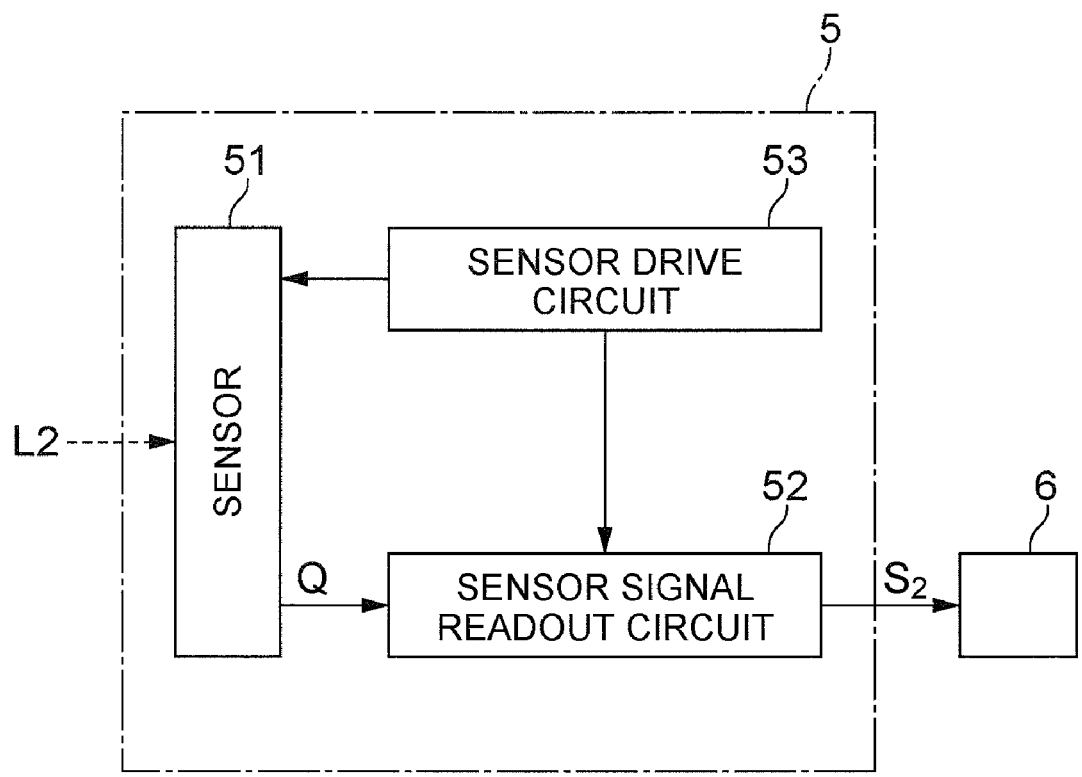
FIG. 2 is a block diagram showing an internal configuration of an imaging section.

FIG. 2 is a block diagram showing an internal configuration of the imaging section 5 in the present embodiment. The imaging section 5 has a sensor signal readout circuit 52 that processes a charge Q read out of the sensor section 51 to generate imaging data $S_2$ and a sensor drive circuit 53 that drives the sensor section 51 and the sensor signal readout circuit 52, in addition to the sensor section 51 described above.

Figure 3:
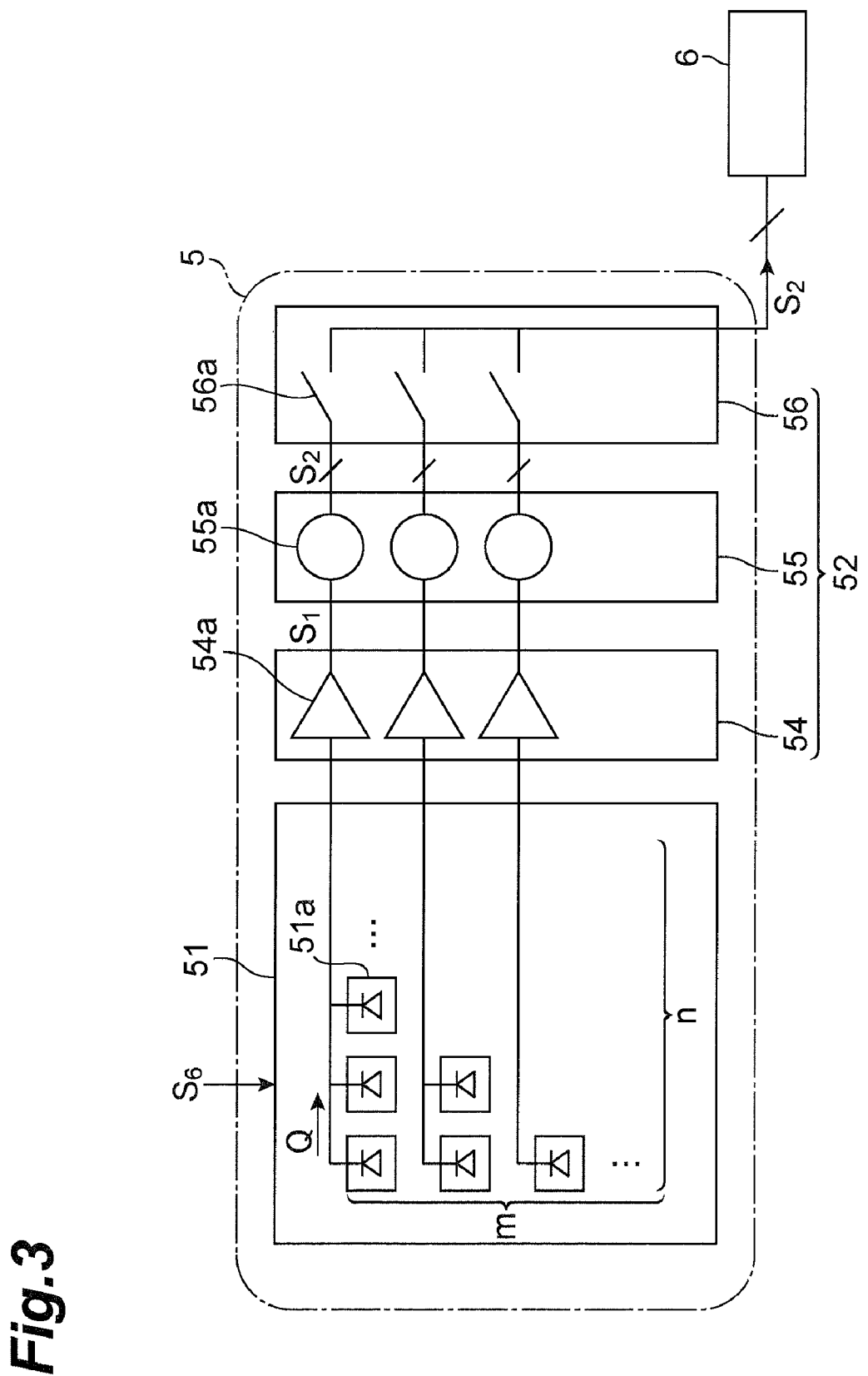
FIG. 3 is a diagram showing a detailed configuration of the imaging section.

FIG. 3 is a diagram showing a detailed configuration of the imaging section 5. The imaging section 5 of the present embodiment is, for example, an imaging device having such a high-speed frame rate as a few hundred Hz to 1 kHz. Examples of such an imaging device include an intelligent vision system (IVS) camera manufactured by Hamamatsu Photonics. By using such an imaging device, small involuntary eye movement of the cornea 101 said to have an oscillation frequency on the order of 100[Hz] can be accurately measured.

The sensor section 51 is a so-called MOS type image sensor, and has a plurality of pixels 51a arrayed two-dimensionally (m rows×n columns). Each of the pixels 51a generates a charge Q according to the amount of incident light. The charges Q are sequentially sent out in accordance with a drive signal $S_6$ from the sensor drive circuit 53. In addition, as the imaging section 5, besides an IVS camera, a high-speed and small-sized two-dimensional semiconductor position detector (a so-called two-dimensional PSD: Position Sensitive Detector), a profile sensor (for example, S9132 manufactured by Hamamatsu Photonics), and the like may be used.

The sensor signal readout circuit 52 includes an amplifier section 54, an A/D converter section 55, and a switch section 56. The amplifier section 54 has m amplifiers 54a corresponding to the number of rows of the sensor section 51. The m amplifiers 54a are electrically connected with corresponding rows of the pixels 51a of the sensor section 51, respectively, and sequentially receive charges Q from the n columns of pixels 51a. The amplifier 54a then amplifies the charge Q and converts the charge Q to an image signal $S_1$, which is a voltage signal.

The A/D converter section 55 has m A/D converters 55a corresponding to the number of rows of the sensor section 51. The m A/D converters 55a are electrically connected to corresponding m amplifiers 54a, respectively, and convert the image signals $S_1$ being voltage signals (analog signals) received from the amplifiers 54a to imaging data $S_2$, which are digital signals. Although the imaging data $S_2$ converted to digital signals is used as imaging data from the imaging section 5 in the present embodiment, the image signals $S_1$ being analog signals may be used as imaging data from the imaging section 5.

The switch section 56 has m switches 56a corresponding to the number of rows of the sensor section 51. The m switches 56a are provided between the corresponding m A/D converters 55a and the bright spot position operation section 6, and control connection/non-connection between the A/D converters 55a and the bright spot position operation section 6 based on a control signal from the sensor drive circuit 53 (refer to FIG. 2). When the switch 56a is brought into a connected state, the imaging data $S_2$ from the A/D converter 55a is provided to the bright spot position operation section 6. The m switches 56a are respectively electrically connected to the bright spot position operation section 6, and individually controlled in terms of connection/non-connection.

Figure 4:
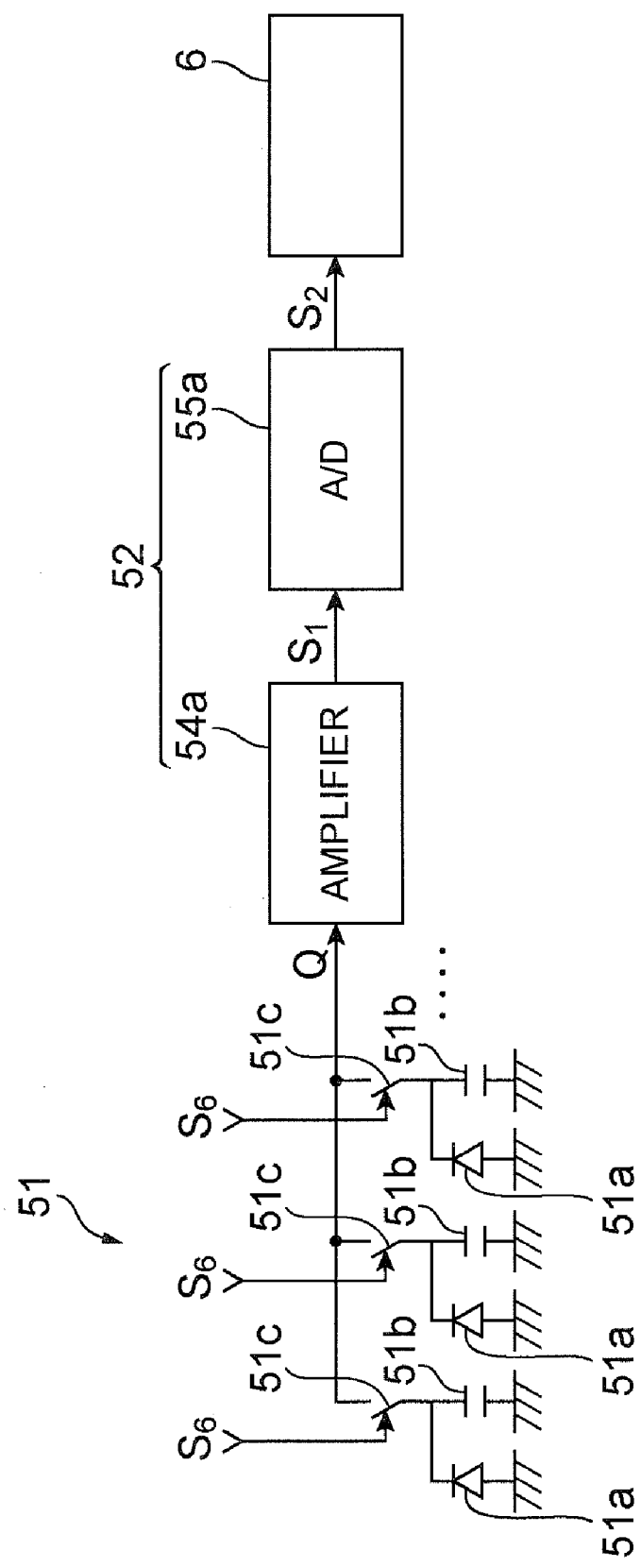
FIG. 4 is a diagram showing an electrical connection relationship between a photodetecting section and an amplifier, an A/D converter, and a bright spot position operation section.

The sensor section 51 and the sensor signal readout circuit 52 will be described in greater detail. FIG. 4 is a diagram showing an electrical connection relationship between the sensor section 51 and the amplifier 54a, the A/D converter 55a, and the bright spot position operation section 6. Referring to FIG. 4, the sensor section 51 has a plurality of pixels 51a consisting of photoelectric conversion elements such as photodiodes. The sensor section 51 further has a plurality of capacitors 51b and a plurality of readout switches 51c corresponding to the pixels 51a.

The photoelectric conversion element of the pixel 51a and the capacitor 51b are connected parallel to each other, and one end of the readout switch 51c is connected to one end of the photoelectric conversion element and capacitor 51b. The other end of the readout switch 51c is, along with the other ends of other readout switches 51c included in the same row, connected to an input terminal of the amplifier 54a. The readout switches 51c are electrically connected to the sensor drive circuit 53 (refer to FIG. 2), and individually controlled in terms of connection/non-connection in accordance with drive signals $S_6$ from the sensor drive circuit 53. An output terminal of the amplifier 54a is electrically connected to an input terminal of the A/D converter 55a, and an output terminal of the A/D converter 55a is electrically connected to the bright spot position operation section 6.

The sensor section 51 and the sensor signal readout circuit 52 shown in FIG. 4 operate as follows. When a corneal reflection light image L2 is made incident on the sensor section 51, a charge according to the amount of incident light of the corneal reflection light image L2 per each pixel 51a is accumulated in the capacitor 51b. When the readout switches 51c are sequentially connected in each row in response to an instruction from the sensor drive circuit 53, charges Q accumulated in the capacitors 51b are sequentially sent to the amplifier 54a.

Figure 5:
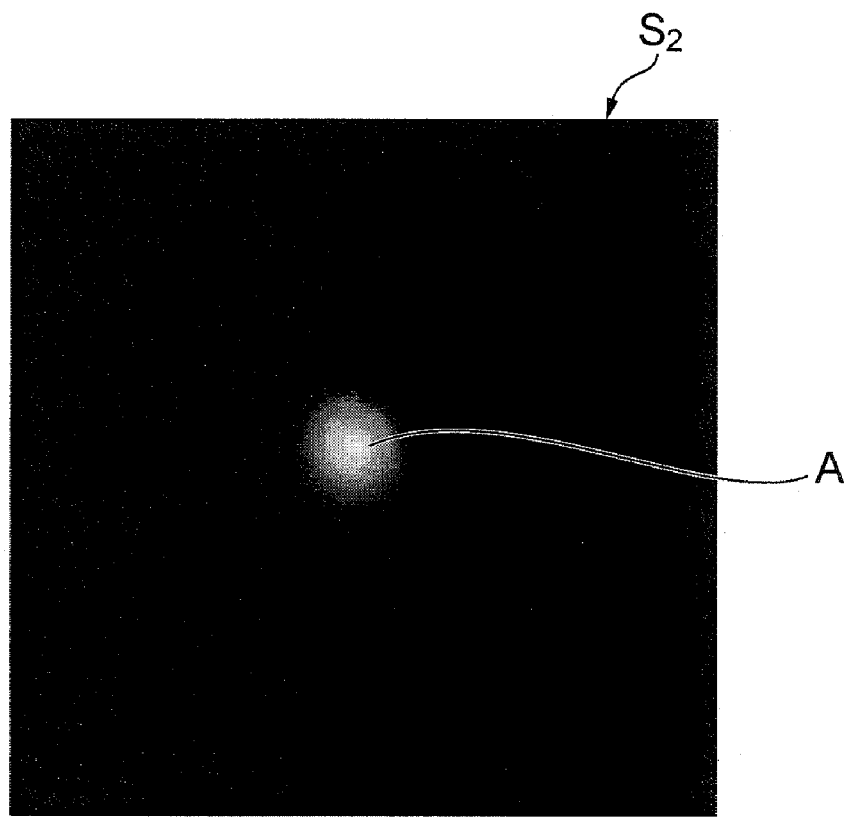
FIG. 5 is a view showing an example of imaging data.

The charge Q is converted to a voltage signal and amplified by the amplifier 54a to become an image signal $S_1$. The image signal $S_1$ is converted by the A/D converter 55a from an analog signal to a digital signal to become imaging data $S_2$. The imaging data $S_2$ is output to the bright spot position operation section 6. FIG. 5 is a view showing an example of the imaging data $S_2$. As shown in FIG. 5, in the imaging data $S_2$, a bright spot A corresponding to the corneal reflection light image L2 is included.

In addition, for speedily performing an operation in the bright spot position operation section 6, it is preferable, for example, that the imaging section 5 further has a parallel operation circuit corresponding to each of the pixels 51a. Such a parallel operation circuit is connected, for example, at a subsequent stage of the A/D converter 55a.

Figure 6:
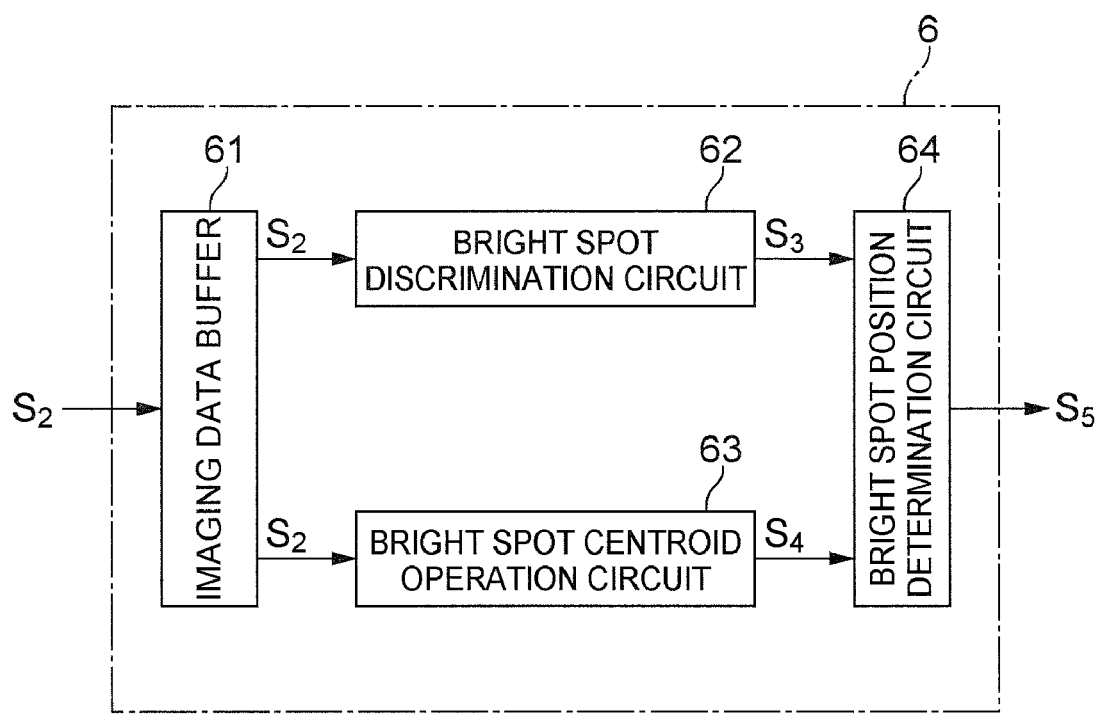
FIG. 6 is a block diagram showing a configuration of the bright spot position operation section.

FIG. 6 is a block diagram showing an internal configuration of the bright spot position operation section 6 in the present embodiment. The bright spot position operation section 6 has an imaging data buffer 61, a bright spot discrimination circuit 62, a bright spot centroid operation circuit 63, and a bright spot position determination circuit 64. The imaging data buffer 61 holds the imaging data $S_2$ provided from the imaging section 5.

The bright spot discrimination circuit 62 discriminates whether a bright spot (corneal reflection light image L2) is included in the imaging data $S_2$ held in the imaging data buffer 61, and generates data $S_3$ indicating a discrimination result. For example, the bright spot discrimination circuit 62 performs a smoothing operation for the imaging data $S_2$ and determines, for each certain region (for example, 3×3 pixels)

in the entire plane of the imaging data $S_2$, whether a central pixel has a certain amount or more of light and indicates a maximal value relative to the surrounding pixels. Then, the bright spot discrimination circuit 62, when any region satisfying these conditions exists, judges that a bright spot is included in the imaging data $S_2$. Specifically, the bright spot discrimination circuit 62 performs the following operations (1) to (3).

(1) Provides the brightness of a pixel position (x,y) (where x=1~n, y=1~m) as D(x,y).
(2) Performs the following operations (2a) and (2 b) for a whole image.
(2a) Smoothing operation: D'(x,y)={D(x−1,y)+D(x+1,y)+D(x,y)+D(x,y−1)+D(x,y+1)}/5
(2b) Discrimination of bright spot: Discriminates a pixel satisfying the condition of D'(x,y)>th and ({D(x,y)>D(x−1, y)} and {D(x,y)>D(x+1,y)} and {D(x,y)>D(x,y−1), D(x, y)>D(x,y+1)}) (where th is a predetermined intensity threshold).
(3) If any pixel satisfying the above condition (2b) exists, it is judged that a bright spot is included in the imaging data $S_2$.

The bright spot centroid operation circuit 63 calculates a centroid of the bright spot in the imaging data $S_2$, and generates data $S_4$ indicating a calculation result. For example, the bright spot centroid operation circuit 63 performs the following operations. That is, the bright spot centroid operation circuit 63 performs a weighting operation for a target image region (whose central pixel position is (Xc,Yc), target image region is (Wx, Wy)), and calculates a centroid of the bright spot of a region judged to be a "bright spot" in the bright spot discrimination circuit 62. Specific operations are as follows.

$$M0=\Sigma(D(X,Y))$$

$$(Xc-Wx/2<X<Xc+Wx/2, Yc-Wy/2<Y<Yc+Wy/2)$$

$$M1x=\Sigma(X\times D(X,Y))$$

$$(Xc-Wx/2<X<Xc+Wx/2, Yc-Wy/2<Y<Yc+Wy/2)$$

$$M1y=\Sigma(Y\times D(X,Y))$$

$$(Xc-Wx/2<X<Xc+Wx/2, Yc-Wy/2<Y<Yc+Wy/2)$$

$$Pos(x)=M1x/M0$$

$$Pos(y)=M1y/M0$$

The bright spot centroid operation circuit 63, as the data $S_4$ indicating a centroid of the bright spot, outputs (Pos(x),Pos(y)) of the above formulae.

The bright spot position determination circuit 64 determines a position of the bright spot based on the existence of a bright spot (data $S_3$) discriminated by the bright spot discrimination circuit 62 and the centroid of the bright spot (data $S_4$) calculated by the bright spot centroid operation circuit 63. The bright spot position determination circuit 64 generates bright spot position data $S_5$ indicating the position of the bright spot, and provides the data to the subsequent tremor signal operation section 7.

Figure 7:
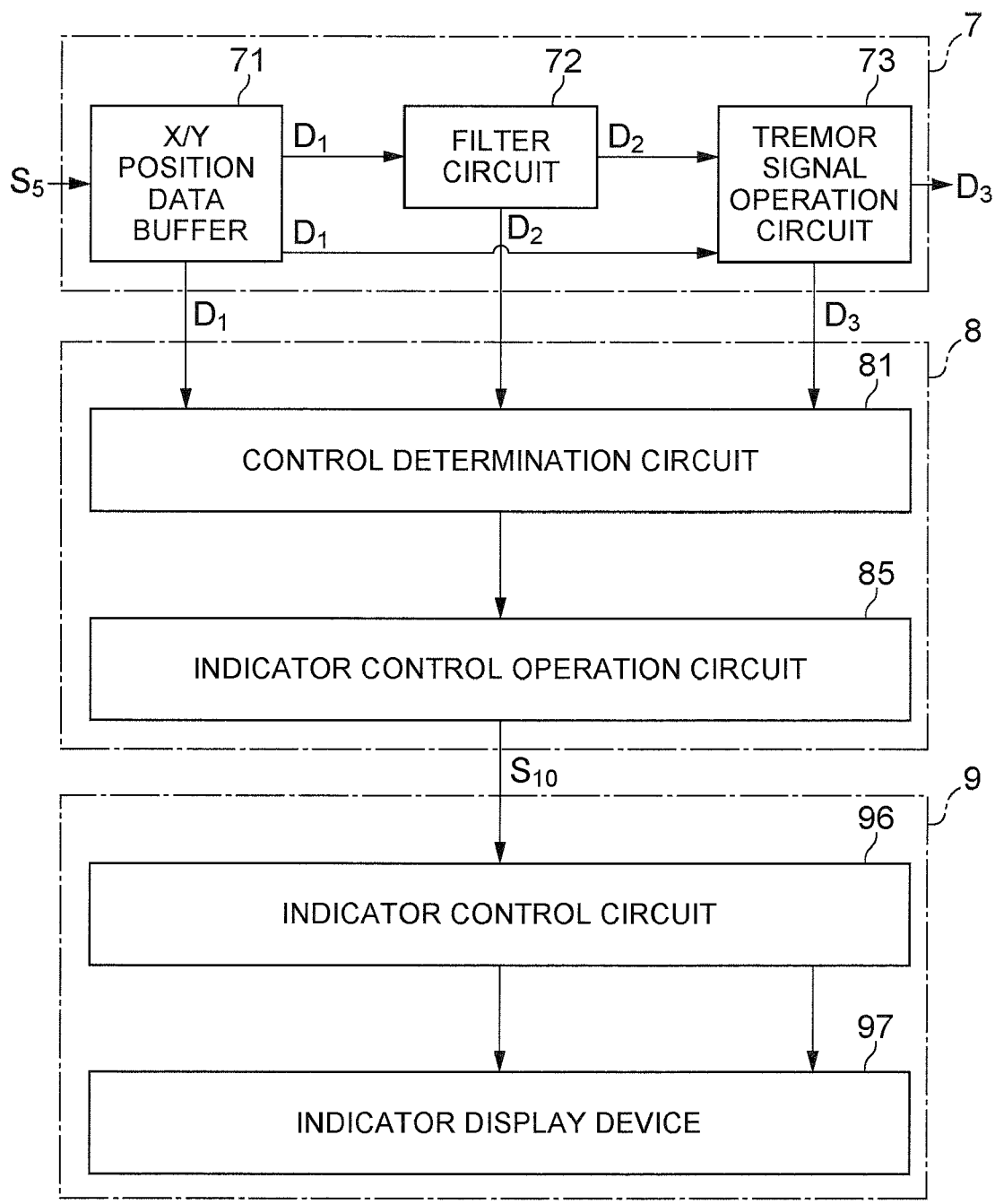
FIG. 7 is a block diagram showing a configuration of a tremor signal operation section, a measurement control operation section, and a measurement control section.

FIG. 7 is a block diagram showing an internal configuration of the tremor signal operation section 7, the measurement control operation section 8, and the measurement control section 9 shown in FIG. 1. As shown in FIG. 7, the tremor signal operation section 7 has a position data buffer 71, a filter circuit 72, and a tremor signal operation circuit 73.

The position data buffer 71 accumulates, as time series data, frame-by-frame bright spot position data $S_5$ provided from the bright spot position operation section 6. This time series data indicates temporal changes in position of the corneal reflection light image L2, and serves as a first data string $D_1$ in the present embodiment. The position data buffer 71 accumulates the bright spot position data $S_5$ for a predetermined period (for example, 1024 frames) to generate the first data string $D_1$, and provides this first data string $D_1$ to both of the filter circuit 72 and the tremor signal operation circuit 73. The filter circuit 72 generates a second data string $D_2$ by smoothing the first data string $D_1$. At that time, a component due to tremor being a high-frequency involuntary eye movement is removed from the first data string $D_1$, and a component due to drift and flick (microsaccade) being low-frequency involuntary eye movements passes through the filter circuit 72.

Figure 8:
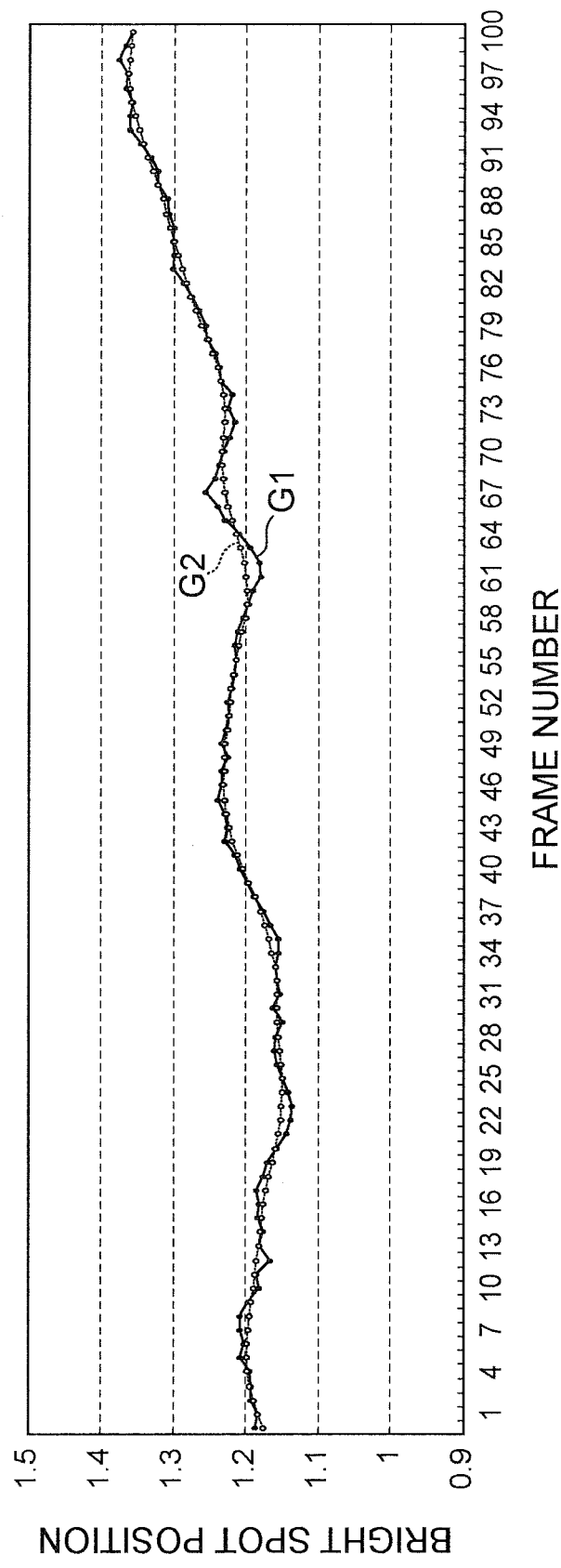
FIG. 8 is a graph showing a typical example of a first data string and a second data string.

FIG. 8 shows a typical example of the first data string $D_1$ and the second data string $D_2$ having been graphed. The vertical axis in FIG. 8 represents the bright spot position, while the horizontal axis represents frames (that is, time). In FIG. 8, as a result of the first data string $D_1$ (graph G1) including a high-frequency tremor component being smoothed, a certain frequency or higher component is removed, and the second data string $D_2$ (graph G2) is generated.

The tremor signal operation circuit 73, by calculating a difference between the first data string $D_1$ and the second data string $D_2$, generates a third data string $D_3$. The tremor signal operation section 7 outputs the thus generated third data string $D_3$ to the outside of the eye movement measurement apparatus 1 as a detection signal concerning the tremor component.

In the eye movement measurement apparatus 1 according to the present embodiment, when imaging data $S_2$ including a corneal reflection light image L2 is generated at a predetermined frame rate by the imaging section 5, a frame-by-frame position of the corneal reflection light image L2 in this imaging data $S_2$ is calculated by the bright spot position operation section 6. Time series data to be thus obtained, that is, a first data string $D_1$ concerning temporal changes in position of the corneal reflection light image L2 is time series data directly indicating movement of the eye 100, and includes both a component due to drift and flick (microsaccade) being low-frequency involuntary eye movements and a component due to tremor being a high-frequency involuntary eye movement.

Then, the first data string $D_1$ is smoothed in the filter circuit 72 to generate a second data string $D_2$. The second data string $D_2$, in which a tremor component has been removed by smoothing, includes mainly a drift component and a flick component. Therefore, by calculating a difference between the first data string $D_1$ and the second data string $D_2$ in the tremor signal operation circuit 73, the drift component and the flick component are favorably removed from the first data string $D_1$, and a data string including mainly the tremor component, that is, a third data string $D_3$ is obtained.

Thus, according to the eye movement measurement apparatus 1 of the present embodiment, a drift component and a flick component can be favorably removed from time series data concerning temporal changes in position of a corneal reflection light image L2 to accurately detect a tremor component.

Here, in the imaging section 5, the bright spot position operation section 6, and the tremor signal operation section 7 described above, such a bright spot as in FIG. 5 is imaged, and its position is measured with an accuracy of 1 μm or less, so that the third data string $D_3$ described above tends to be superimposed with a high-frequency noise resulting from measurement conditions such as a position of the indicator 11 and a focal position, in addition to the component resulting from movement of the cornea 101.

A component due to such noise, because of its relatively high frequency, is likely to be removed along with a tremor component when the first data string $D_1$ is smoothed. As a result, such a noise component is included in the third data string $D_3$ along with the tremor component, which contributes to preventing an improvement in detection accuracy of a tremor component. Therefore, by optimizing each measurement condition so as to reduce the high-frequency noise in the third data string $D_3$, the measurement accuracy of the tremor component can be further improved. Accordingly, the eye movement measurement apparatus 1 of the present embodiment further includes the measurement control operation section 8 and the measurement control section 9 as measurement condition control means.

The measurement control operation section 8 has a control determination circuit 81 and an indicator control operation circuit 85. The control determination circuit 81 receives the first to third data strings $D_1$ to $D_3$ from the tremor signal operation section 7 and calculates, based on these data strings $D_1$ to $D_3$, a parameter for evaluating a signal to noise ratio (hereinafter, referred to as an S/N ratio) in the third data string $D_3$.

Examples of the parameter for evaluating the S/N ratio in the third data string $D_3$ include the following. One example is a ratio (Pp/Pb) or a difference (Pp−Pb) between a local maximum value Pp and a local minimum value Pb of intensity in a frequency analysis waveform of the first data string $D_1$. It suffices when the size of this ratio (Pp/Pb) or difference (Pp−Pb) is larger than a predetermined value (or is maximized) to determine a measurement condition to be satisfactory, and to continue (fix) the measurement condition.

Figure 9:
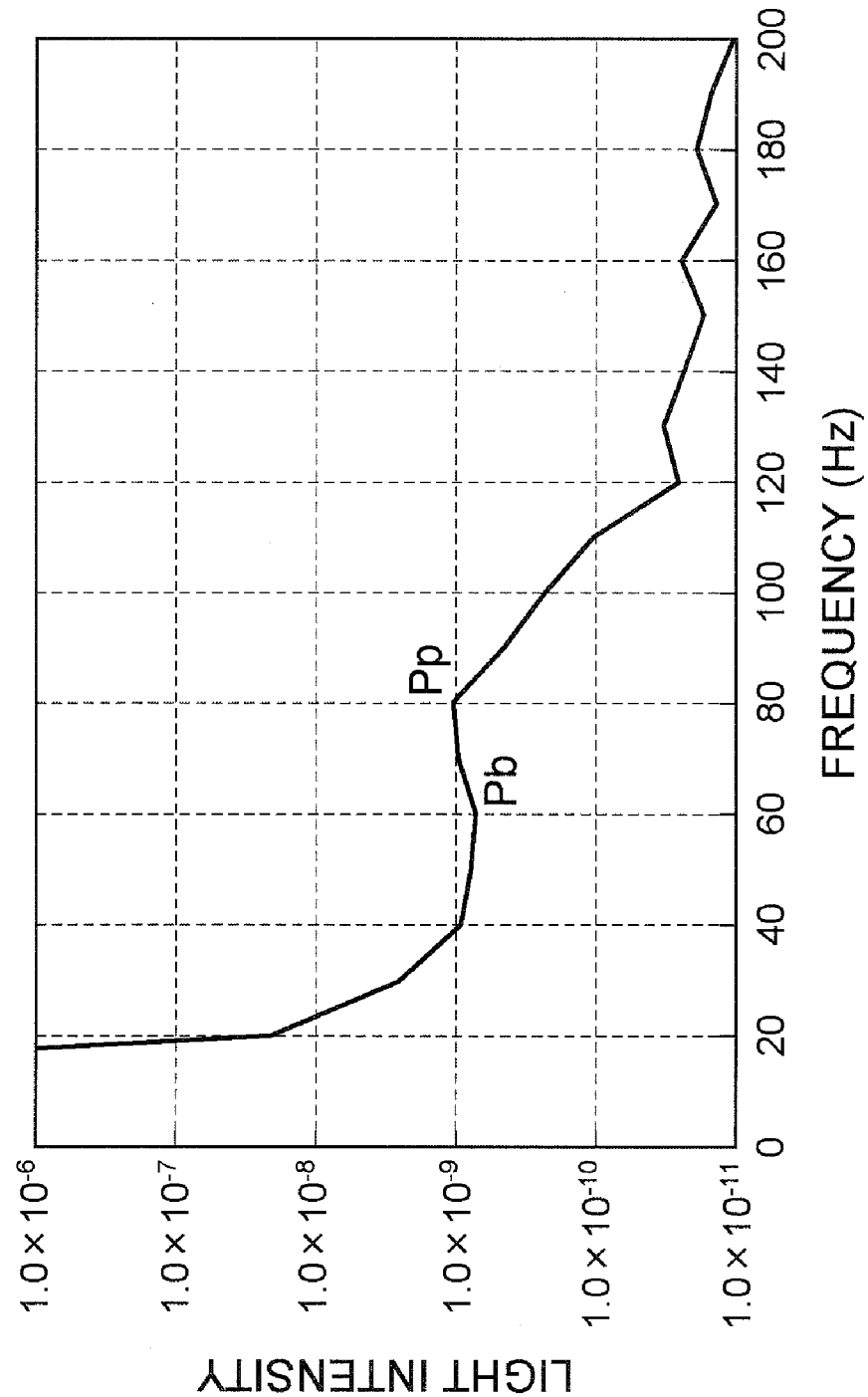
FIG. 9 is a graph showing an example of the result of a frequency analysis applied to the first data string.

FIG. 9 is a graph showing an example of the result of a frequency analysis applied to the first data string $D_1$. In this graph, the local maximum value Pp of the intensity appears around 80 Hz, indicating an involuntary eye movement (tremor). Moreover, the local minimum value Pb of the intensity appears around 50 Hz. When the ratio (Pp/Pb) or difference (Pp−Pb) of these extremal values is larger than a predetermined value (for example, 1.2) (or is maximized), because the noise component included in the first data string $D_1$ is small, the S/N ratio in the third data string $D_3$ consequently becomes high. Therefore, by fixing the measurement condition in such a case, the noise component included in the third data string $D_3$ can be reduced to detect a tremor component more accurately.

Moreover, another example is a feature quantity based on a velocity or an acceleration of a bright spot calculated from the second data string $D_2$. This feature quantity is, for example, a velocity and acceleration of a bright spot (that is, a velocity and acceleration of drift and flick included in a corneal movement), a velocity average value and acceleration average value of a bright spot (that is, a velocity average value and acceleration average value of drift and flick), or standard deviations of a velocity and acceleration of a bright spot. It suffices when such a feature quantity is smaller than a predetermined value that the control determination circuit 81 determines a measurement condition to be satisfactory, and continues (fixes) the measurement condition.

Moreover, still another example is a total value (or an average value) of velocity amplitudes (that is, velocity amplitudes of tremor included in a corneal movement) of a bright spot based on the third data string $D_3$, and it suffices when this total value (or average value) is smaller than a predetermined value (or is minimized) to determine a measurement condition to be satisfactory, and to continue (fix) the measurement condition.

Figure 10:
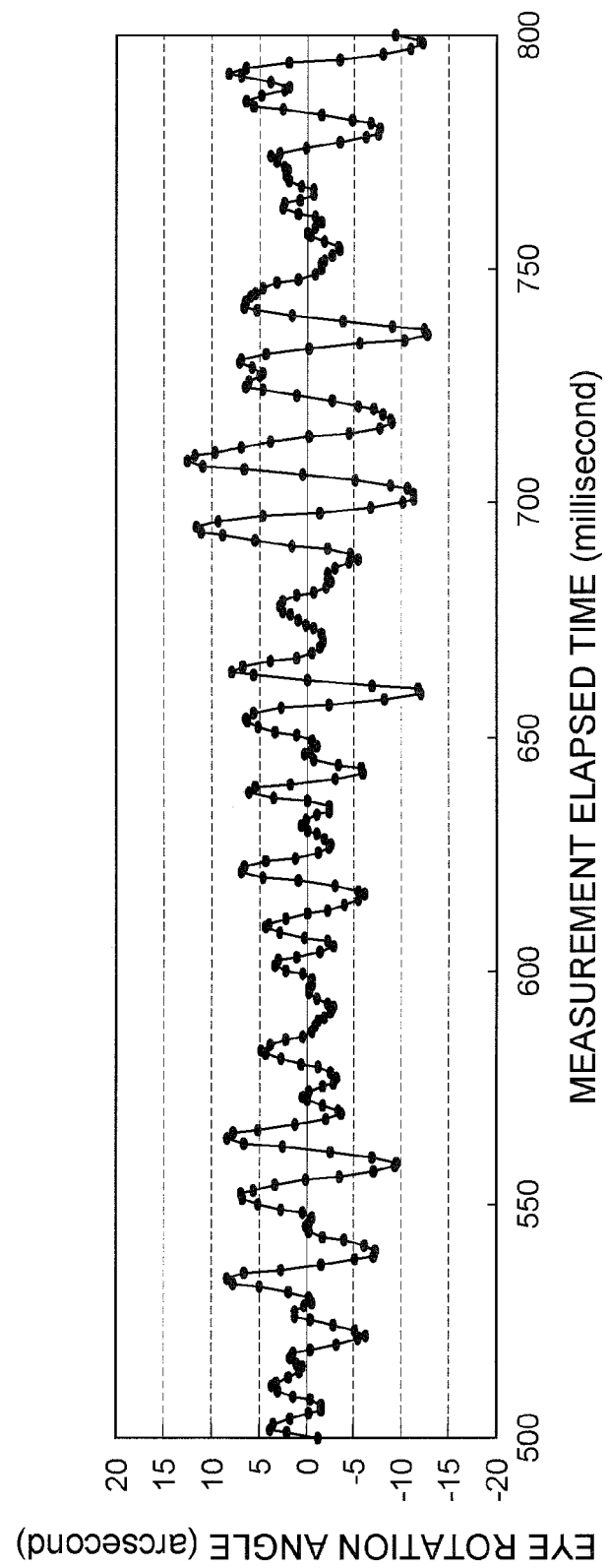
FIG. 10 is a graph showing temporal changes in the velocity of tremor included in movement of a cornea, calculated based on a third data string.

FIG. 10 is a graph showing temporal changes in the velocity of tremor included in movement of the cornea, calculated based on the third data string $D_3$. The control determination circuit 81 calculates, in such a graph, an amplitude total value (or amplitude average value) of the tremor velocity, and continues (fixes) the measurement condition when this value is smaller than a predetermined value (or is minimized). Thereby, the noise component included in the third data string $D_3$ can be reduced to detect a tremor component more accurately.

Referring again to FIG. 7, the indicator control operation circuit 85 calculates, of the measurement conditions in the eye movement measurement apparatus 1, a control amount concerning a position and a focus of the indicator 11 based on the parameter supplied from the control determination circuit 81. The operation result in the indicator control operation circuit 85 is sent to an indicator control circuit 96 of the measurement control section 9 as a control signal $S_{10}$, and the indicator control circuit 96 controls the position and focus of the indicator 11 through an indicator display device 97. For example, when the indicator 11 includes a plurality of infrared LEDs different in position from each other, the indicator control circuit makes any of the LEDs selectively emit light.

Figure 11:
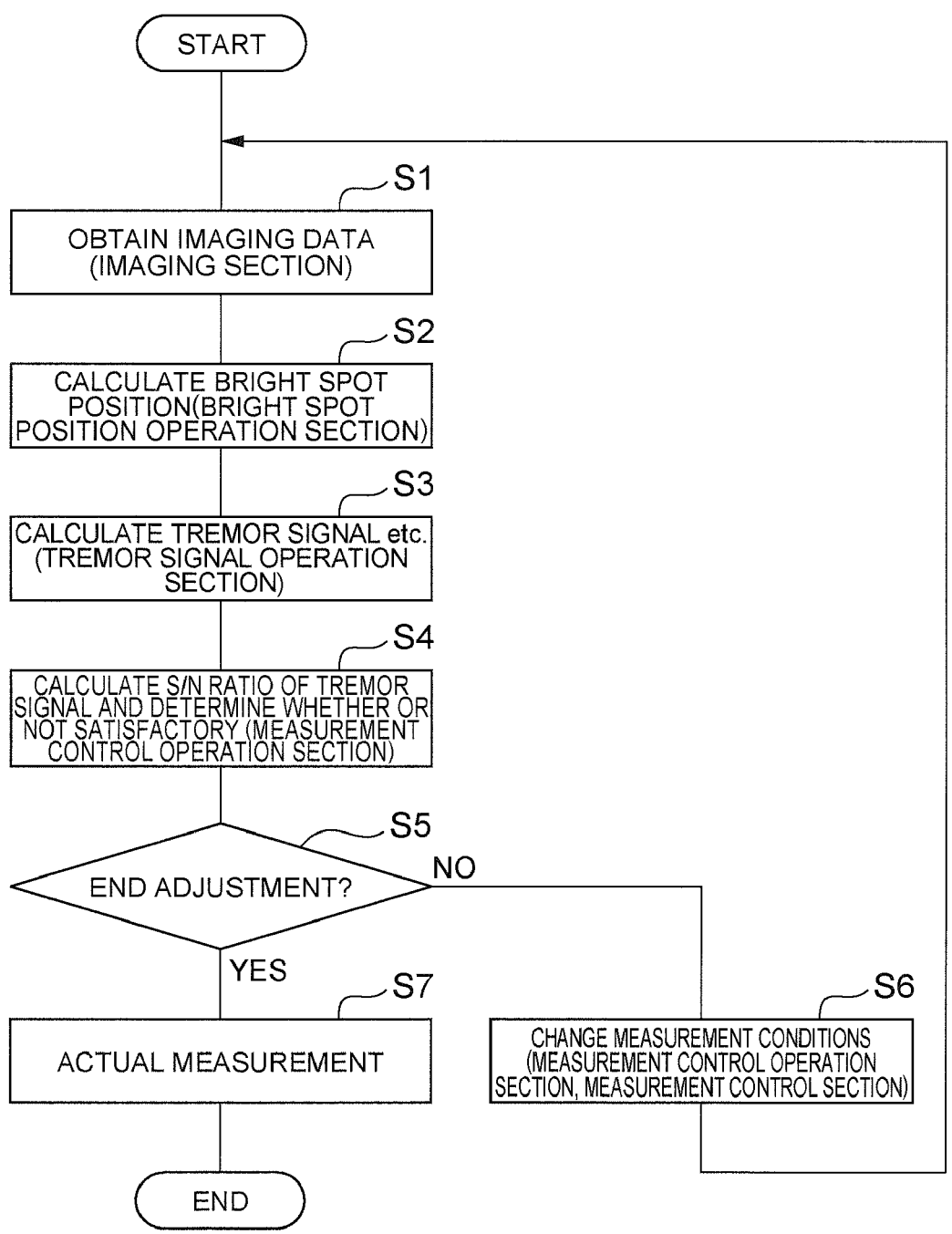
FIG. 11 is a flowchart showing an operation for optimizing the measurement conditions so that a high-frequency noise in the third data string is reduced.

FIG. 11 is a flowchart showing an operation for optimizing the measurement conditions so that a high-frequency noise in the third data string $D_3$ is reduced. First, the imaging section 5 obtains imaging data $S_2$ (step S1), and the bright spot position operation section 6 then calculates a bright spot position in the imaging data $S_2$ (step S2). Subsequently, the tremor signal operation section 7 generates a first data string $D_1$, a second data string $D_2$, and a third data string $D_3$ (step S3).

Subsequently, the measurement control operation section 8, based on these data strings $D_1$ to $D_3$, calculates a parameter for evaluating an SN ratio in the third data string $D_3$. The measurement control operation section 8 evaluates a value of this parameter by a comparison or the like with a predetermined value (step S4), and when the parameter value is not satisfactory ("No" in step S5), the operation section calculates a control amount concerning the position and focus of the indicator 11, and adjusts the position and focus of the indicator 11 through the measurement control section 9 (step S6). Then, after step S6, the operation of step S1 onward in the foregoing is again performed. Moreover, when the parameter value is satisfactory ("Yes" in step S5), the operation section ends optimization of the measurement conditions to start a measurement (actual measurement) of a tremor component (step S7).

The eye movement measurement apparatus according to the present invention is by no means limited to the embodiment mentioned above, and can be variously modified in other ways. For example, in the above embodiment, an infrared LED is used as the lighting device, but another light source may be used. Moreover, the measurement condition control means (the measurement control operation section 8 and measurement control section 9) of the above embodiment are configured so as to control all of the intensity of infrared light to be irradiated onto a cornea, the position of an infrared light source, the focus of infrared light, and the position and focus of the indicator based on the parameter, but may be configured so as to control at least one of these measurement conditions based on the parameter.

Moreover, there has been in the above description "the second data string $D_2$, in which a tremor component has been removed by smoothing", but as a method for obtaining a waveform excluding a high-frequency component, in place of the average method mentioned here, a "low frequency filter" by filtering using frequency analysis means such as a Fourier analysis or a wavelet analysis may be used.

Here, in the eye movement measurement apparatus according to the above embodiment, used is an eye movement measurement apparatus that measures movement of a cornea by imaging a corneal reflection light image generated as a result of irradiating the cornea with light, including: an imaging section having a photodetecting section including a plurality of pixels arrayed two-dimensionally, for generating imaging data including the corneal reflection light image made incident in the photodetecting section; bright spot position operation means that calculates a position of the corneal reflection light image in the imaging data; and tremor signal operation means that generates a third data string indicating a tremor component included in movement of the cornea by calculating a difference between a first data string concerning temporal changes in position of the corneal reflection light image and a second data string obtained by smoothing the first data string.

Moreover, the eye movement measurement apparatus may further include an indicator at which a subject is made to gaze; and measurement condition control means that calculates a parameter for evaluating a signal to noise ratio in the third data string, and controls at least one measurement condition of a position and a focus of the indicator based on the parameter.

In the eye movement measurement apparatus, an indicator at which a subject is made to gaze is sometimes provided in order to control movement of the cornea. In such a case, noise resulting from measurement conditions concerning the indicator, such as the position and focus of the indicator tends to be superimposed on the first data string. A component due to such noise, because of its relatively high frequency, is likely to be removed along with a tremor component when the first data string is smoothed. As a result, such a noise component is included in the third data string along with the tremor component, which contributes to preventing an improvement in detection accuracy of a tremor component. Therefore, by calculating a parameter for evaluating a signal to noise ratio in the third data string, and controlling at least one of a position and a focus of the indicator based on the parameter, the noise component included in the third data string can be reduced to detect a tremor component more accurately.

Moreover, it may be possible in the eye movement measurement apparatus that the parameter is a ratio or a difference of a local maximum value and a local minimum value of intensity in a frequency analysis waveform of the first data string. This allows favorably evaluating the signal to noise ratio in the third data string. In this case, it may be possible in the eye movement measurement apparatus that the measurement condition control means fixes the at least one measurement condition when the ratio (Pp/Pb) or the difference (Pp−Pb) between the local maximum value Pp and the local minimum value Pb of intensity in the frequency analysis waveform of the first data string is larger than a predetermined value. This allows effectively reducing the noise component included in the third data string.

Moreover, it may be possible in the eye movement measurement apparatus that the parameter is a feature quantity based on a velocity or an acceleration of the cornea to be calculated from the second data string. This allows favorably evaluating the signal to noise ratio in the third data string. In addition, the feature quantity in this case is, for example, a velocity and acceleration of the cornea calculated from the second data string, an average value and standard deviation of the corneal velocity, or an average value and standard deviation of the corneal acceleration. Moreover, in this case, it may be possible in the eye movement measurement apparatus that the measurement condition control means fixes the at least one measurement condition when the feature quantity is smaller than a predetermined value. This allows effectively reducing the noise component included in the third data string.

Moreover, it may be possible in the eye movement measurement apparatus that the parameter is a total value of velocity amplitudes of the cornea based on the third data string. This allows favorably evaluating the signal to noise ratio in the third data string. In this case, it may be possible in the eye movement measurement apparatus that the measurement condition control means fixes the at least one measurement condition when the total value of velocity amplitudes of the cornea based on the third data string is smaller than a predetermined value. This allows effectively reducing the noise component included in the third data string.

INDUSTRIAL APPLICABILITY

The present invention can be used as an eye movement measurement apparatus capable of accurately detecting a tremor component.

The invention claimed is
1. An eye movement measurement apparatus that measures movement of a cornea by imaging a corneal reflection light image generated as a result of irradiating the cornea with light, comprising:
  an imaging section having a photodetecting section including a plurality of pixels arrayed two-dimensionally, for generating imaging data including the corneal reflection light image made incident on the photodetecting section;
  bright spot position operation means that calculates a position of the corneal reflection light image in the imaging data; and
  tremor signal operation means that generates a third data string indicating a tremor component included in movement of the cornea by calculating a difference between a first data string concerning temporal changes in position of the corneal reflection light image and a second data string obtained by smoothing the first data string.

2. The eye movement measurement apparatus according to claim 1, further comprising:
  an indicator at which a subject is made to gaze; and
  measurement condition control means that calculates a parameter for evaluating a signal to noise ratio in the third data string, and controls at least one measurement condition of a position and a focus of the indicator based on the parameter.

3. The eye movement measurement apparatus according to claim 2, wherein the parameter is a ratio or a difference of a local maximum value and a local minimum value of intensity in a frequency analysis waveform of the first data string.

4. The eye movement measurement apparatus according to claim 3, wherein the measurement condition control means fixes the at least one measurement condition when the ratio (Pp/Pb) or the difference (Pp−Pb) between the local maximum value Pp and the local minimum value Pb of intensity in the frequency analysis waveform of the first data string is larger than a predetermined value.

5. The eye movement measurement apparatus according to claim 2, wherein the parameter is a feature quantity based on a velocity or an acceleration of the cornea to be calculated from the second data string.

6. The eye movement measurement apparatus according to claim 5, wherein the measurement condition control means fixes the at least one measurement condition when the feature quantity is smaller than a predetermined value.

7. The eye movement measurement apparatus according to claim 2, wherein the parameter is a total value of velocity amplitudes of the cornea based on the third data string.

8. The eye movement measurement apparatus according to claim 7, wherein the measurement condition control means fixes the at least one measurement condition when the total value of velocity amplitudes of the cornea based on the third data string is smaller than a predetermined value.

* * * * *